US009943699B2

(12) United States Patent
Souder

(10) Patent No.: US 9,943,699 B2
(45) Date of Patent: Apr. 17, 2018

(54) THERAPEUTIC MAGNET APPARATUS

(76) Inventor: James J. Souder, Bracey, VA (US)

( * ) Notice: Subject to any disclaimer, the term of this patent is extended or adjusted under 35 U.S.C. 154(b) by 696 days.

(21) Appl. No.: 12/940,610

(22) Filed: Nov. 5, 2010

(65) Prior Publication Data
US 2011/0133872 A1   Jun. 9, 2011

Related U.S. Application Data

(63) Continuation-in-part of application No. 11/818,956, filed on Jul. 9, 2004, now abandoned.

(51) Int. Cl.
*H01F 7/00* (2006.01)
*A61N 2/06* (2006.01)
*H01F 7/02* (2006.01)
*A61N 2/00* (2006.01)

(52) U.S. Cl.
CPC .............. *A61N 2/06* (2013.01); *H01F 7/0294* (2013.01); *A61N 2/008* (2013.01)

(58) Field of Classification Search
CPC ...................................................... A61N 2/06
USPC ........................................ 335/298, 302, 306
See application file for complete search history.

(56) References Cited

U.S. PATENT DOCUMENTS

| | | | | |
|---|---|---|---|---|
| 3,233,950 A | * | 2/1966 | Baermann | 310/90.5 |
| 3,899,762 A | * | 8/1975 | Studders | 335/302 |
| 3,921,620 A | * | 11/1975 | Nakayama | 600/15 |
| 4,544,904 A | * | 10/1985 | Tarachand | 335/302 |
| 4,587,956 A | * | 5/1986 | Griffin et al. | 600/15 |
| 4,599,826 A | * | 7/1986 | Podoprigora | 451/177 |
| 5,134,374 A | * | 7/1992 | Breneman et al. | 324/319 |
| 5,194,810 A | * | 3/1993 | Breneman et al. | 324/319 |
| 5,313,182 A | * | 5/1994 | Blache | 335/306 |
| 5,707,333 A | * | 1/1998 | Bakst | 600/9 |
| 5,871,438 A | * | 2/1999 | Ardizzone | 600/9 |
| 5,900,793 A | * | 5/1999 | Katznelson et al. | 335/296 |
| 5,938,579 A | * | 8/1999 | Cavazos | 492/8 |
| 5,984,855 A | * | 11/1999 | DiNapoli | 600/15 |
| 6,104,271 A | * | 8/2000 | Barrett | 335/306 |
| 6,157,281 A | * | 12/2000 | Katznelson et al. | 335/306 |
| 6,304,162 B1 | * | 10/2001 | Nakatsuka et al. | 335/302 |
| 6,322,491 B1 | * | 11/2001 | Bove et al. | 600/15 |
| 6,344,021 B1 | * | 2/2002 | Juster et al. | 600/15 |
| 6,348,033 B1 | * | 2/2002 | Catlett | 600/15 |
| 6,360,457 B1 | * | 3/2002 | Qui et al. | 36/140 |
| 6,383,129 B1 | * | 5/2002 | Ardizzone et al. | 600/9 |
| 6,525,634 B2 | * | 2/2003 | Laskaris et al. | 335/296 |
| 6,600,401 B2 | * | 7/2003 | Zuk et al. | 335/299 |
| 6,646,530 B2 | * | 11/2003 | Ruhrig | 335/306 |
| 6,652,446 B1 | * | 11/2003 | Bove et al. | 600/15 |
| 6,773,391 B1 | * | 8/2004 | Bricot | 600/15 |
| 6,828,890 B2 | * | 12/2004 | Cope et al. | 335/296 |
| 6,846,379 B1 | * | 1/2005 | Bove et al. | 156/272.4 |

(Continued)

*Primary Examiner* — Alexander Talpalatski
(74) *Attorney, Agent, or Firm* — Avery N. Goldstein; Blue Filament Law, PLLC

(57) ABSTRACT

A reconfigurable magnetic therapy apparatus is formed by multiple magnetic magnetic components which are maintained in a stable planar array by either mutual magnetic attraction or mechanical fixtures which may include a ferromagnetic backing plate to which the elements are magnetically attached. The array can be separated and reconfigured by the user to provide different magnetic patterns that favor either high surface strength, or deep penetration, or multiple smaller sub arrays to treat multiple sites.

6 Claims, 8 Drawing Sheets

(56) References Cited

U.S. PATENT DOCUMENTS

| | | | |
|---|---|---|---|
| 6,859,123 B2* | 2/2005 | Zheng et al. | 335/296 |
| 2004/0140204 A1* | 7/2004 | Navala et al. | 204/298.2 |
| 2006/0005427 A1* | 1/2006 | Wang et al. | 36/25 R |

* cited by examiner

THERAPEUTIC MAGNET APPARATUS

CROSS-REFERENCE TO RELATED APPLICATIONS

This application is a continuation-in-part of U.S. patent application Ser. No. 11/818,956 filed Jul. 9, 2004, herein incorporated by reference in its entirety.

BACKGROUND OF THE INVENTION

1. Field of the Invention

The present invention relates to magnet arrays that are used to deliver magnetic therapeutic fields to tissue in plants and animals. In particular a plurality of discrete shaped magnetic elements can be combined to form a single magnet array comprising discrete magnetic zones which may be of like polarity or mixed polarity. The overall polarization of the single magnet array can be varied by positioning the poles of each of the magnetic elements to be either North or South. Thus to obtain like polarity in the magnet array the polarity of each of the magnetic elements that comprise the array would be positioned to either North or South. Another embodiment according to the present invention comprises moats or spacer elements of non-magnetic material positioned in between each of the magnetic elements that comprise the magnet array.

2. Description of Related Art

Curative, and also prophylactic, magnetic field treatment is well known in the art. For example, it is known that magnetic bands covering the lower back can be effective in reducing pain originating in the lower back, and that a magnetic bracelet worn on the wrist can reduce pain or stiffness originating in the wrist. It is also known that the application of magnetic devices directly to the site of other painful body parts such as elbows or ankles can reduce pain in those parts. These known methods all typically involve the use of permanent magnets.

Many patents have been issued for therapeutic magnets including patents for concentric circle magnetic patterns impressed into flexible magnet material by relatively simple methods using permanent magnet fixtures or electrical discharge magnetizing fixtures. The resultant magnets typically have residual magnetic fields of 750 Gauss to 3,000 Gauss and can be created in a field of under 10,000 Gauss, which is achievable with neodymium or other high power permanent magnet fixtures. The problem with that method is that the power required to magnetize a concentrically arranged high power permanent magnet such as neodymium iron boron is too high.

Monolithic composite high power "Hard" magnet concentric patterns are difficult to achieve, because it is not practical using current technology to impress concentric magnetic zones of opposite polarity onto a wafer of homogeneous high power magnet material such as neodymium iron boron. Nominally 40,000 Gauss is required to coerce the field in neodymium. Additionally once a particular polarization pattern is impressed onto a wafer that polarization pattern can only be modified by subjecting the wafer to the same process that was used to originally impress the magnetic zones onto it.

Some practitioners believe that one magnetic pole has a different therapeutic effect than the other. For example some practitioners prefer to use a magnetic array having an all North polarization when treating a given condition. A technical obstacle present when constructing concentric patterns of a multi-element single pole array using high power permanent magnets is that magnetic disks of like polarity in the same plane mutually repel each other.

Thus a need exists for a high power permanent magnet device that can be configured into concentric patterns of either like or mixed polarities and an efficient way to construct concentric patterns with permanent high power magnets regardless of like or mixed polarity magnetic distribution.

SUMMARY OF THE INVENTION

An apparatus according to present invention comprises arranging multiple high power permanent magnetic elements to form a single magnetic array such that the single magnetic array can deliver more flux per unit volume and can deliver optimum penetration. Optimum penetration means projected field distance from the surface and magnetic intensity at a given depth. In mixed pole devices it is possible to trade increased depth of penetration for diminished surface intensity or visa versa.

An embodiment according to the present invention comprises multiple high power permanent magnets that are concentrically arranged such that adjacent zones of polarity mutually reinforce the magnetic field of one another resulting in increased Gauss readings at the surface of the magnet.

Another embodiment according to the present invention comprises multiple high power permanent magnets and a removable backer plate comprised of a suitable ferromagnetic material to which a permanent magnet is strongly attached or magnetic stainless steel.

Another embodiment according to the present invention comprises varying the thickness of some of the multiple high power magnets such that when the magnets are arranged concentrically in a like polarity array onto a removable ferromagnetic backer plate, the thinner of the high power magnets comprising the array will be subject to less expulsive force from neighboring magnets and will cling tighter to the backer plate.

Another embodiment according to the present invention comprises a concentric array of multiple high power magnets having a moat or a zone of magnetically transparent material positioned in between adjacent high power magnets such that flux returning around a periphery of a magnet will exert around the periphery of a magnet minimum cancellation or reinforcement of flux exiting the plane of the adjacent magnets. In the case of like pole neighboring magnets, there will be mutual cancellation of the proximal zones, and the moat will appear to be a zone of opposite polarity. In the case of a moat placed between elements of opposite polarity, the result will be increased field projection of the active magnet zones due to diminished blending of opposite fields above the surface of the array.

Another embodiment according to the present invention comprises a concentric array of multiple high power magnets having additional magnets with their North and South poles positioned perpendicular in between each of the high power magnets such that the additional magnets have an East or West polarization relative to the North or South polarization of each of the multiple high power magnets.

Another embodiment according to the present invention comprises constructing alternating pole magnets out of more powerful magnetic materials such as samarium cobalt, neodymium iron boron magnets or other materials that may become available that can deliver more flux per unit volume than common ferrite magnets.

A further embodiment according to the present invention comprises a magnetic composite of concentric rings, disks or other geometric shapes that can be assembled with either pole of any element facing the subject at the discretion of the user.

A magnetic apparatus is provided that includes a mechanical fastener. Multiple magnets simultaneously engage the mechanical fastener so as to retain the magnets in a planar array between two of the magnets. With removal of the mechanical fastener, one of the multiple magnets is readily inverted about a rotation axis and reassembled to provide a reoriented apparatus.

The above and yet other aspects and advantages of the present invention will become apparent from the hereinafter set forth Brief Description of the Drawings and Detailed Description of the Invention.

BRIEF DESCRIPTION OF THE DRAWINGS

Apparatus that are particular embodiments of the invention will now be described, by way of example, with reference to the accompanying diagrammatic drawings.

DETAILED DESCRIPTION OF THE PREFERRED EMBODIMENTS

The apparatus according to present invention comprise adjacently or concentrically configuring a plurality of high power permanent magnets such that the array can deliver more flux per unit volume and can deliver optimum penetration characteristics.

An inventive process is provided for adjusting magnetic field characteristics projecting from a magnetic treatment apparatus. An animal such as a human; domesticated animal such as racehorse, dog, cat, cow, and sheep; a water source; a foodstuff; or a plant represents a treatment subject that is readily subjected to such magnetic treatment. According to an inventive process, multiple magnets are provided in an initial pattern either in a package or otherwise. At least one of the magnets is repositioned to define a reoriented array with different magnetic field characteristics projecting therefrom relative to the initial pattern. It is appreciated that one or more magnets are readily removed from the initial pattern and simultaneously applied to the same or different test subject to represent multiple treatment apparatuses created by moving discrete magnets from the initial pattern. It is appreciated that because the magnets are separable, a wide array of reoriented arrays is readily formed. By way of example, a reoriented array that is a planar array is well suited for application to, or being brought into magnetic treatment proximity to, a treatment subject. Additionally, such a planar array is readily modified to include additional magnets stacked onto the plane defined by the base array. The reoriented array is also readily formed as a concentric array. Gaps created between the individual magnets of the reoriented array are readily filled with a magnetically transparent spacer or a magnetically permeable spacer. To facilitate structural integrity of the reoriented pattern, a mechanical fastener is optionally provided. The mechanical fastener readily takes the form of a variety of pins simultaneously engaging multiple magnets or a ferromagnetic backing plate to which the magnets are attached.

Figure 10:
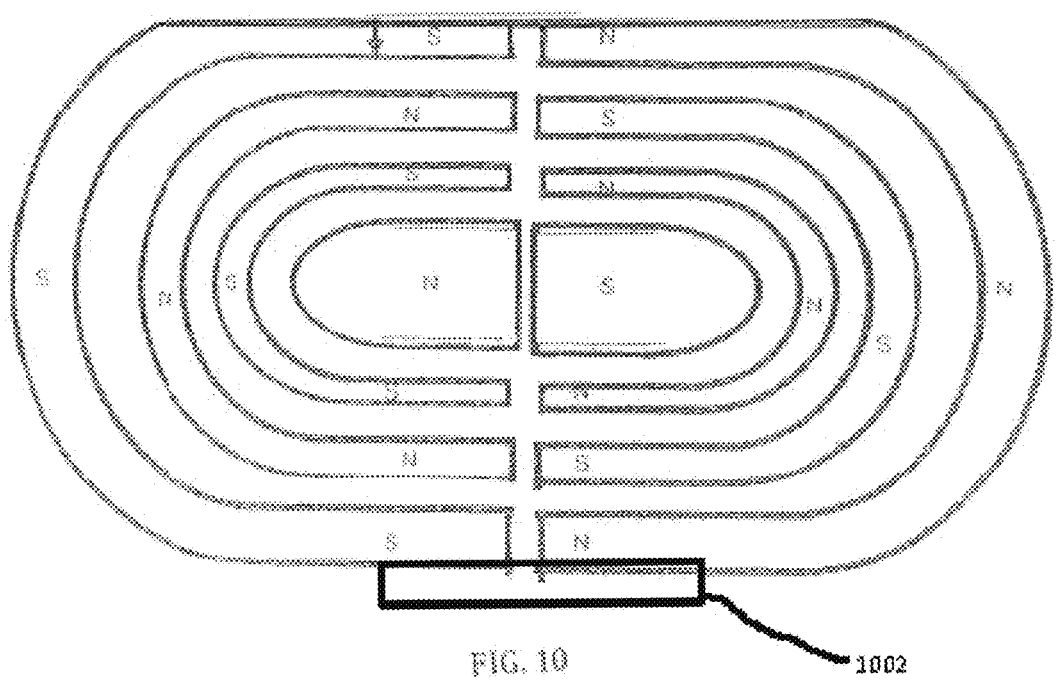
FIG. 10 illustrates a concentric array of semi-circular high power magnets according to an embodiment of the present invention.

According to the present invention, a plurality of such discrete magnets along with a securement 1002 as shown in FIG. 10 such as hook and loop fastener, a contact adhesive or a ferromagnetic garment clip for sandwiching a garment are provided for retaining the magnets as an array and are included to provide an apparatus suitable to retain the array in proximity to a subject in need of magnetic therapy. Garments illustratively include clothing and a bandage. In a preferred embodiment the magnets of a therapeutic device collectively weigh less than one International pound (16 ounces). Alternatively, a securement 1002 as used herein is a pad or pillow in which the device is embedded. The pad or pillow containing the therapeutic device is then placed in proximity to the subject in need of therapy.

A magnetic apparatus according to the present invention is also provided based on a first magnet that has a circumference of a given linear extent. A second magnet of opposite polar orientation is secured and intended for non-movement relative to the first magnet that encompasses the first magnet around the majority of the circumference such that the combined first and second magnet field is greater than 4,000 surface Gauss near their junction for an apparatus having a thickness of 0.32 centimeters. These high magnetic field strengths afford superior magnetic biotherapy relative to those of the prior art. In specific embodiments thereof, the first magnet is completely encompassed by the second magnet of opposite polarity and, more specifically, the first and second magnets are concentric and maintain planar orientation by mutual magnetic attraction. In another embodiment, a substantially planar reconfigurable magnetic therapy apparatus includes a common fixture to which a first magnet having a planar geometric shape and a second magnet abutting the edge of the first magnet are retained in planar alignment by mutual magnetic attraction or mechanical attachment to the fixture by magnetic or mechanical means. A securement secures the first magnet and the second magnet in proximity to a subject in need of therapy. It is appreciated that at least one additional magnet are readily retained in planar alignment with the first magnet and the second magnet. The magnets can be of such an apparatus can be arranged in a number of configuration including concentric, and non-nested patterns. Exemplary non-nested patterns includes stripes and capital Greek letter omega shapes (Ω) that are commonly referred to as horseshoe-shaped.

The benefits of concentric circle magnet arrays are believed by many practitioners to derive from blood vessels crossing over zones of opposite polarity. Additionally a concentric pattern is an ideal geometric pattern to permit a pole arrangement where the flux emanating from a central pole magnetic element or any given orbital ring can arc over on the arched trajectory of a flux line and descend on a magnetic element adjacent to it. After the flux reaches its apex it returns toward the plane from which it originated. When the flux returns to the plane from which it originated it is now going in the opposite direction. Thus a Gauss meter would ascribe the zone it travels through on the downward portion of the arc as having a polarity opposite to its originating polarity on the upward portion of the arc. For example, if a rocket taking off is being described as going North on take-off it would be described as going South after reaching the zenith of its arc trajectory for its return trip to the ground surface from which it departed. Since it has an arc trajectory the rocket would land some given lateral distance away from its starting point.

Figure 1:
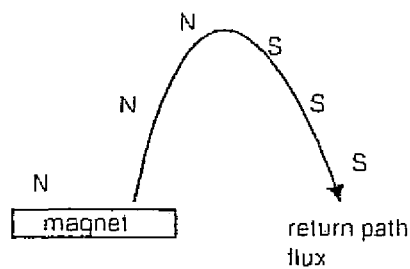
FIG. 1 is a diagram of a return path of a magnetic flux line flow.

Referring to FIG. 1 which illustrates a magnet 101 having a North polarity on a first surface 102 and a South polarity on a second surface 103. Flux lines that exit from each atom in a magnet follow a trajectory similar to the rocket example described above. Flux exits the first surface with an ascending portion of the arc called North 104 reaches an apex then returns to the surface plane some lateral distance away with a descending portion of the arc called South 105.

Figure 2:
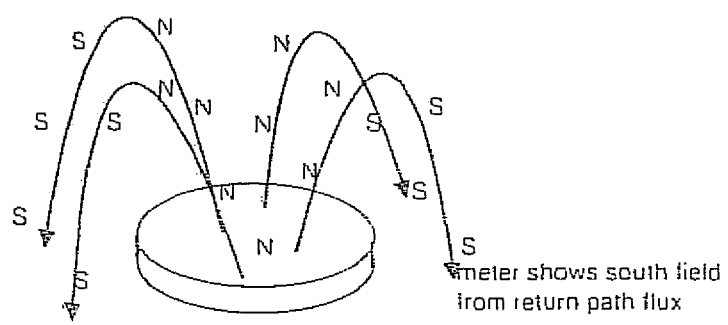
FIG. 2 is a diagram of return paths of multiple flux lines.

FIG. 2 illustrates magnetic flux radiation. Magnetic flux 201 radiates 360 degrees in all directions from any given magnetic body or element 202.

Figure 3:
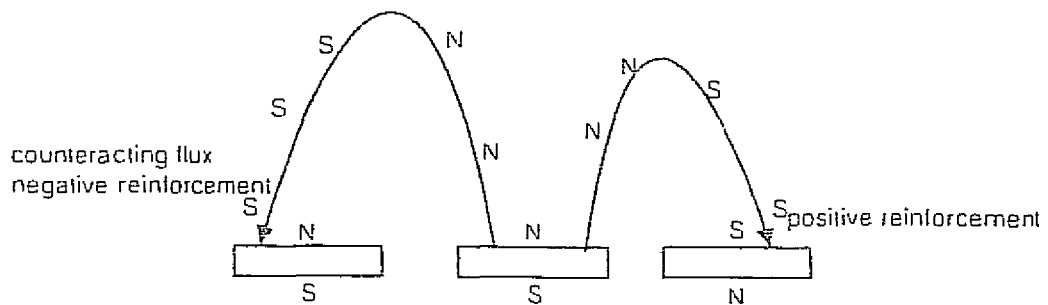
FIG. 3 is a diagram depicting reinforcement and counteraction of magnetic fields due to magnetic return flux lines from adjacent magnetic elements.

FIG. 3 illustrates reinforcement and counteraction of flux lines originating from a magnetic array. A first magnetic element 301 comprises a first surface 302 having a North polarity and a second surface 303 having a South polarity. Adjacent to the first magnetic element 301 is a second magnetic element 304 comprising a first surface 305 having a North polarity and a second surface 306 having a South polarity. Adjacent to the second magnetic element 304 is a third magnetic element having a first surface 307 having a South polarity and a second surface 308 having a North polarity. When the downside of an arc of a flux line 309 passes through a zone of like polarity, the field is reinforced since the flux line 309 is going the same direction as neighboring flux lines entering surface 307. When the downside of an arc of a flux line 311 lands in an area of a different polarity 302 it counteracts and cancels the effect of a North flux line since it is now South bound on the downside of the arc 311 and weakens the field at the surface 312.

Figure 4:
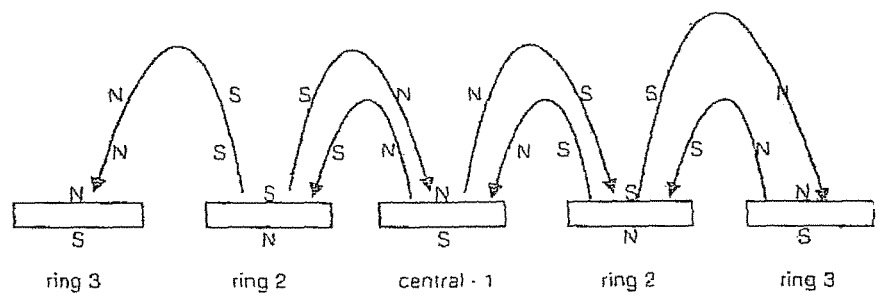
FIG. 4 is a side view of a concentric magnet arrangement having mixed polarities according to an embodiment of the present invention.

FIG. 4 illustrates a cross section of a plane of a concentric magnet array. Flux emanating from a bull's eye 401 of an archery target type magnet will create a ring of concentric second poles 402 around the bull's eye 401. In this illustration the second pole is South. If a second concentric ring 403 is magnetized as South the magnetic field will be reinforced from the flux emanating from the bull's eye 401. This process is repeated in a third concentric ring 404 in which the South flux 405 arising from the second concentric ring 403 returns to the plane of origin in both the bull's eye 401 and third concentric ring 404 as North. Since the bull's eye and the third concentric rings are oriented as North, the Gauss level measurement at the surface is considerably increased by the reinforcement. By contrast if the bull's eye 401 and the third concentric ring 404 were oriented as South, the surface Gauss levels would be decreased by an exact amount of the return flux or downward arc from like pole neighboring zones.

A method of constructing an array of magnetic elements in a concentric pattern according to an embodiment of the present invention comprises forming each magnetic element into various sized washer shaped disks or solid disks then assembling the disks to form an array of nested or concentric patterns. Additionally if the adjacent zone of a disk is of opposite polarity to a disk next to it the disks will automatically align as each disk is mutually pulling on the zones of the adjacent disks next to it. Thus a mixed pole magnet array having a magnetic element similar to a bull's and concentric magnetic element disks surrounding the bull's eye form a pattern in a plane similar to the orbiting rings of the planet Saturn. An advantage to the above method of construction is that each magnetic zone emanating from a disk reinforces the magnetic field of its neighboring disk's magnetic zone near the surface. This results in an order of magnitude increase of Gauss readings at the surface of the magnet array as compared to Gauss readings taken from a magnet array of all one polarity however less penetration will occur at a distance above the surface where mixed North and South flux self cancel.

Figure 5:
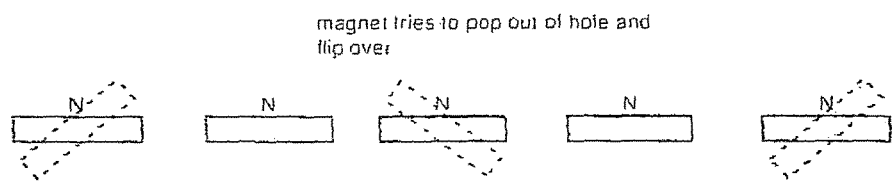
FIG. 5 depicts like polarized magnets repelling one another according to an embodiment of the present invention.

FIG. 5 illustrates magnetic repulsion of like poles. Some practitioners prefer to use a magnetic array having an either all North or all South polarization when treating a given condition. These practitioners prefer to forgo extra surface strength of alternating pole arrays in favor of a single pole array for example all North. According to an embodiment of the present invention to construct a single pole concentric magnet array adjacent magnetic element rings would be oriented all in the same pole direction. However when constructing a concentric array of magnets using magnetic disks 501 having like poles in proximity to one another in one plane, the magnetic disks 501 resist such an orientation by mutually repelling each other 502. An embodiment according to the present invention comprises a means of holding together adjacent magnetic elements of like polarity in one plane when a magnet array is assembled whereby the natural propensity of like pole oriented disks to separate and be expelled from the surface or break apart forcefully is overcome by magnetic adhesion to the ferromagnetic backer plate. This is important in non-contiguous shapes like parallel stripes or squiggles that do not have inherent containment. (Described below with reference to FIGS. 12, 13, and 14).

Figure 6:
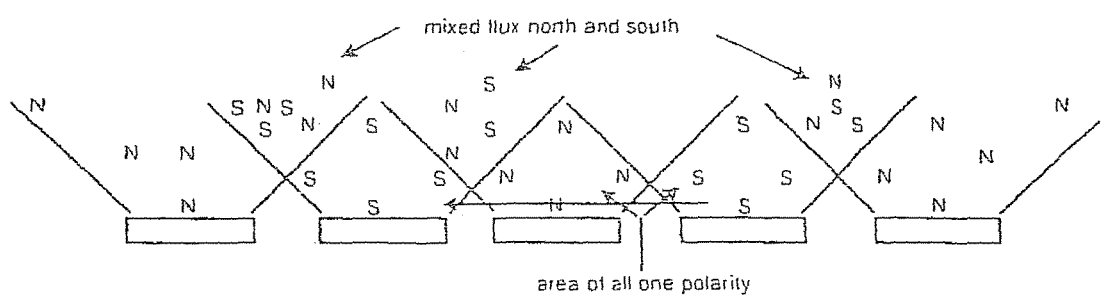
FIG. 6 depicts mixed North flux and South flux emanating from a concentric configuration of magnets according to an embodiment of the present invention.

FIG. 6 illustrates mixed fluxes that occur in mixed pole magnet arrays. Alternating pole magnetic elements 601 are assembled into a concentric magnet array. At a distance above the surface of the alternating pole magnetic elements 601 flux from adjacent North and South pole zones mix 602 thereby canceling out the field of their opposite pole neighboring magnetic zones. Thus alternating pole magnet arrays do not project their magnetic field as far as they would if the adjacent pole magnetic zone was either of like polarity or was not magnetized at all. The zone over each pole face is reinforced 603. The return flux from neighbors reinforces as well.

Figure 7:
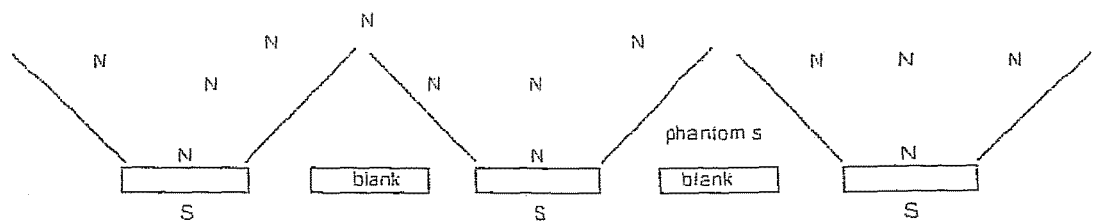
FIG. 7 illustrates flux flow from a concentric high power magnet array having moats according to an embodiment of the present invention.

FIG. 7 illustrates an all North pole magnet array having blank spacers that is spacers made of non-magnetic material positioned in between adjacent magnets. If the adjacent magnetic elements 701 are either like pole or moats 702 such as blank non-magnetic elements or air gaps, a magnet array can be configured for optimum penetration. Penetration means projected field distance from a surface of the array. Using moats 702 permit a given quantum of magnet to project farther than the same mass in one intact geometry due to the minimizing of self cancellation effects.

Figure 8:
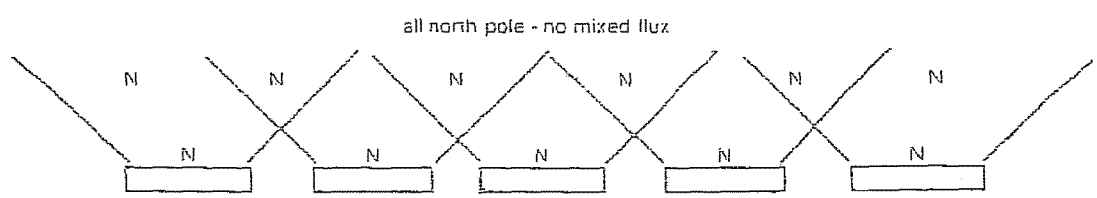
FIG. 8 illustrates flux flow from a like polarization array of high power magnets according to an embodiment of the present invention.

FIG. 8 illustrates an all North pole magnet array. The magnet array can be assembled using the same symmetrical geometric shaped magnetic elements 801 oriented in a like pole direction to enhance penetration that were used to configure a mixed pole version of a magnet array. A backer plate that facilitates holding the array together mechanically is illustrated below in FIG. 13.

Figure 9:
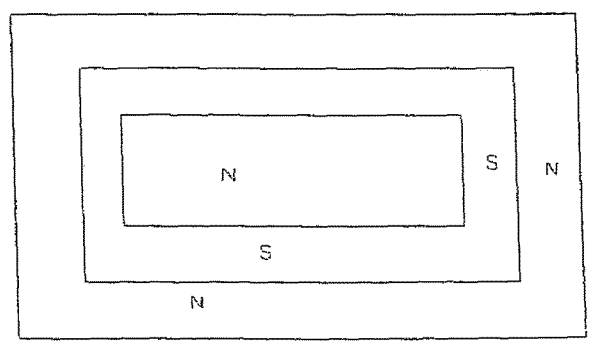
FIG. 9 illustrates a non-circular shape concentric array of magnets according to an embodiment of the present invention.

FIG. 9 illustrates a non-circular concentric magnetic array. A magnet array formed from any nested geometric shape including squares 901, rectangles, stars and even irregular shapes such as hearts and kidneys can be constructed according to an embodiment of the present invention. For maximum flexibility of reconfiguring the array, symmetrical geometric shapes permit each magnetic element to be turned over and still be assembled into a magnetic array having the same shape. The difference being whether the polarity on the surface of the magnetic array is like or mixed. Additionally non-symmetrical geometric shapes may be used to configure an array.

FIG. 10 illustrates a composite magnet array. The composite magnet array is comprised of circular or elliptical shapes having two or more magnetic components 1001. A basic circular or elliptical magnetic element is divided into at least two magnetic components 1001. The at least two magnetic components 1001 can be assembled by mixing their polarity such that zones of opposite polarity 1002 will attract each other and the entire composite magnetic array will bond together by mutual attraction. An advantage to this embodiment according to the present invention is that each of the two halves or smaller units can be applied to different treatment areas. The composite magnet as a whole will have more intense gradient delta or contrasting values of magnetic intensity attributable to more boundary crossings within the magnetic zone. This will result in higher surface Gauss levels being achieved. A fluid passing through the magnetic zone will encounter more boundary crossings thereby resulting in greater electromotive force in the case of ions which will be kinetically engaged by the magnetic field reversal. Moving charged particles through magnetic field reversals impart beneficial kinetic energy that result in enhanced chemical reactions among ions.

Figure 11:
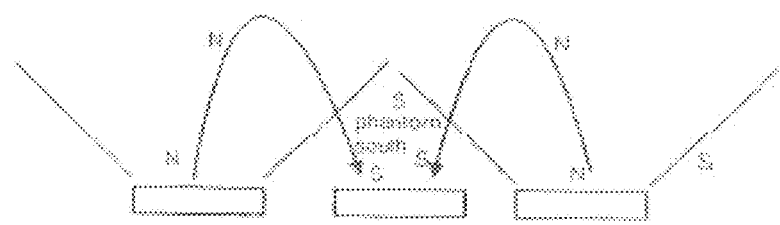
FIG. 11 illustrates phantom South polarization according to an embodiment of the present invention.

FIG. 11 illustrates a magnet array having blank spacers and varying magnetic element widths. The size of individual elements determines field projection and surface Gauss values for any given thickness of magnetic material. Typically in a symmetrical alternating pole pattern having uniform widths across the cross section of sequential orbits, the field projection will be largely attenuated by mixing of the fields at a distance of nominally one section's width above the surface. By adjusting section width of the magnetic elements 1101 such that greater magnetic element pole widths will be used when more penetration is desired, a magnetic array can be constructed to maximize magnetic performance at different projections. It also depicts a phantom opposite pole that manifests in the blank zone which is flanked by like pole magnets.

A phantom magnetic zone of opposite polarity will be detected by a Gauss meter in the moat and there will not be any cancellation of fields due to the fact that the moat is not magnetically oriented material and does not emit any magnetic flux. This advantageously results in a greater projected field emanating from the magnet array since all magnetic elements have like poles that are projecting in the same direction. Thus the return flux falls harmlessly into the moat thereby increasing the net total quantity of flux projected into the subject tissue.

Figure 12:
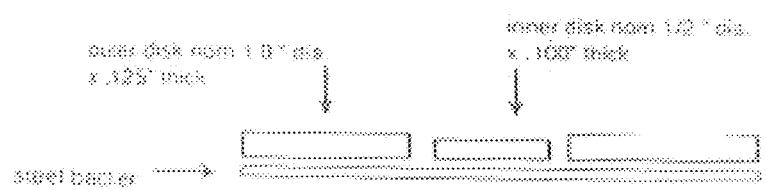
FIG. 12 illustrates a concentric array of varying thicknesses of magnets according to an embodiment of the present invention.

FIG. 12 illustrates a magnet array according to an embodiment of the present invention. A backer plate 1201 is employed to hold the magnetic elements 1202 and 1203 together in one plane. The backer plate is comprised of ferromagnetic material such that either like and mixed polarity arrays will adhere to the backer plate 1201. The backer plate provides the advantage that the integrity of the array in like polar configurations will be maintained.

Since magnetic strength weakens geometrically with the distance from the pole surface, intermediate distances from paint thickness or protective coatings can weaken the magnetic strength sufficiently such that when a like pole magnetic element 1203 is positioned in a bull's eye position of a like pole array, the like pole magnetic element 1203 will naturally try to eject itself from the like pole magnet array due to magnetic repulsion. In some instances, such as with a gap due to paint or a thin backer plate, the like pole magnetic element 1203 cannot be coerced to remain firmly in place by virtue of its attraction to the backer plate. The repulsion tendency of the like pole magnetic element 1203 can be overcome by constructing the like pole magnetic element 1203 out of a slightly thinner section of magnet, such that the like pole magnetic element 1203 will be sucked down by its attraction to the backer plate 1202 into the bull's eye position. Similarly orbital rings may also be made thinner. According to an embodiment of the present invention the typical size of a neodymium or other high strength magnetic element will range from ½ to 2 inches across with a nominal thickness of 0.060 to 0.150 inches however other size magnetic elements can be used.

Figure 13:
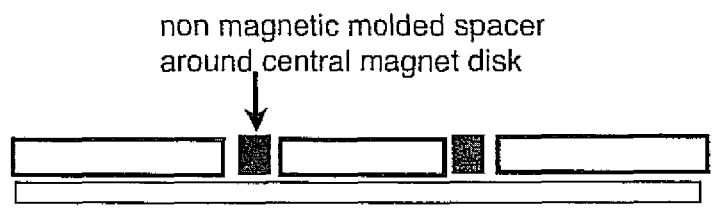
FIG. 13 illustrates a concentric array of magnets having a ferromagnetic backer plate according to an embodiment of the present invention.

FIG. 13 illustrates a boundary moat according to an embodiment of the present invention. A boundary moat comprising an integrally molded spacer or a removable concentric spacer of non-magnetic material 1301 for array stability surrounds the like pole magnetic element that will form a bull's eye 1302 of a magnet array. However the boundary moat can also be an air-gap. The integrally molded spacer or removable concentric spacer 1301 can be used in a magnet array to provide a blank moat inside a ring of a given polarity into which return flux (Described above in FIGS. 1 through 4) can land without counteracting and degrading a magnetic field of an adjacent magnet. Advantageously this further allows maintaining the unidirectional orientation of all poles (like pole array) that many practitioners prefer. The blank space or moat can be filled with either a disk of ferromagnetic material that will remain locked into a magnetic array by magnetic attraction or alternatively a non-magnetic element such as plastic, wood, ceramic, or non-ferrous metal can be substituted for the moat such that the mechanical stability of the complete array is maintained. A blank space or air-gap can be substituted for the spacer without loss of efficiency. An array of intermittent concentric zones of like polarity maximizes the contribution of the magnetic elements in an array having like polarities since the cancellation of return flux from neighboring magnetic zones is minimized. The spacing from the adjacent zone of like polarity will enable the clamping force of the like pole magnetic element to overcome the repulsion of neighboring like pole zones. Preferably the magnet array comprises two magnetic elements and a backer plate. The first of the two elements is positioned within the bull's eye of the array and the second magnetic element is positioned to surround the first magnetic element, both the first and second magnetic elements adhere to the backer plate. Any number of successive orbits can be added.

Figure 14A:
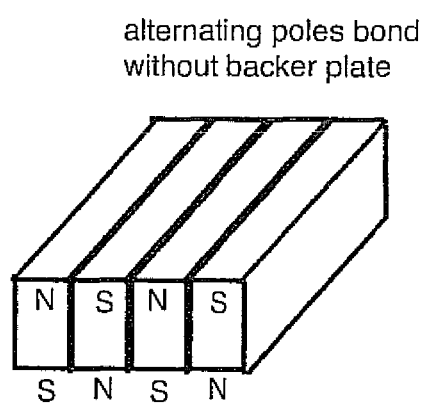
FIG. 14A illustrates a like pole array according to an embodiment of the present invention.
Figure 14B:
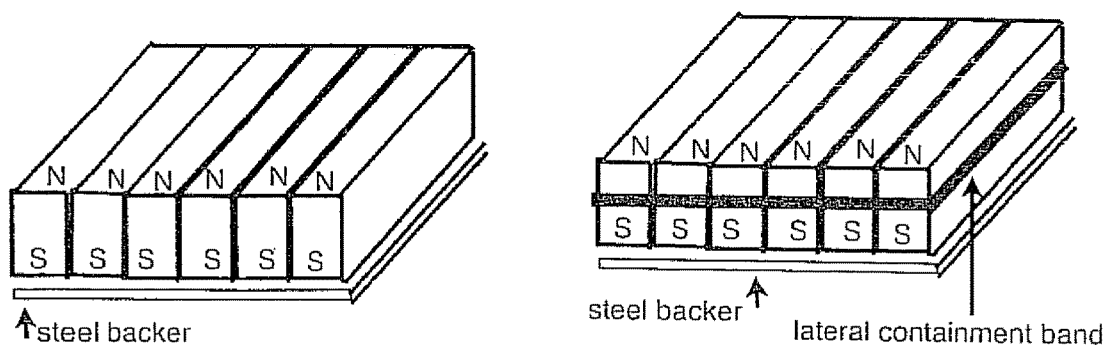
FIG. 14B illustrates a mixed pole array according to an embodiment of the present invention.

FIGS. 14A and 14B illustrate like and mixed pole magnet arrays. Referring to FIG. 14A according to an embodiment of the present invention sequential adjacent magnetic element arrays can be constructed using geometric shapes other than circles. Arrays of rectangles 1401, squares and even non-linear geometric shapes can be configured. A peripheral ring of tensile banding material 1402 or end caps of opposite pole magnetic material would be required to confine like pole magnet arrays that would have a natural tendency to separate and disperse if held in a given plane by attraction to a common ferromagnetic backing plate 1403. Such magnet arrays could include magnetically inert blanks or any pole orientation desired by a user. Additionally referring to FIG. 14B the magnet array can be comprised of mixed poles 1404 wherein the array would self-adhere due to magnetic attraction and would not require a peripheral ring of tensile banding material for mechanical stability.

Figure 15:
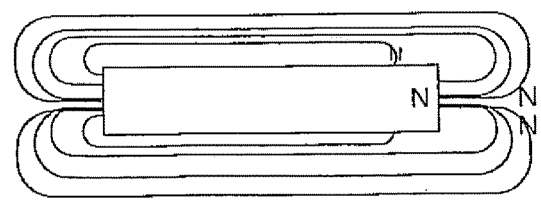
FIG. 15 illustrates flux lines emanating from a magnet in East West orientation.

FIG. 15 illustrates an East West magnetic pole alignment. In addition to North South pole orientations and magnetically blank elements, a magnetic field can be oriented in what is called an East West alignment. The East West pole alignment comprises poles facing parallel rather than perpendicular to a plane on which a magnet array is assembled. The East West alignment results in at least the same total quantity of flux passing through subject tissue. Since flux 1501 emanating from one end of a bar magnet makes a loop and reverses direction traveling down a side of a magnet and returns to its point of origin, the distribution of flux must be measured with the aperture of a Hall effect detector having its window perpendicular to a side of the magnet. It is an erroneous conclusion that there is no magnetic flux on the sides of a bar magnet. This conclusion often arises during flux measurement due to the aperture of a Hall effect detector being placed perpendicular rather than parallel to a side of the bar magnet. This is analogous to a sailboat having its sail aligned with the wind as opposed to the sail being aligned broadside to the wind which will capture and measure the real force of the wind. Therapeutic magnet arrays having East West orientation will deliver the same flux dosages to subject tissue with a slightly different intensity profile.

An inventive magnet apparatus is illustrated with respect to FIGS. 16-19 and characterized by a mechanical stabilization of a magnet array to provide a spaced-apart relationship between the component magnets while providing for reconfiguration of the inventive magnet apparatus. While FIGS. 16-19 illustrate in prototypical form novel aspects of the invention, it is appreciated that additional magnets are readily provided to create more complex arrays of magnet apparatuses. It is further appreciated that an inventive magnet apparatus readily incorporates a combination of mechanical configuration stabilizers amenable to disassembly and reorientation of the element magnets.

Figure 16:
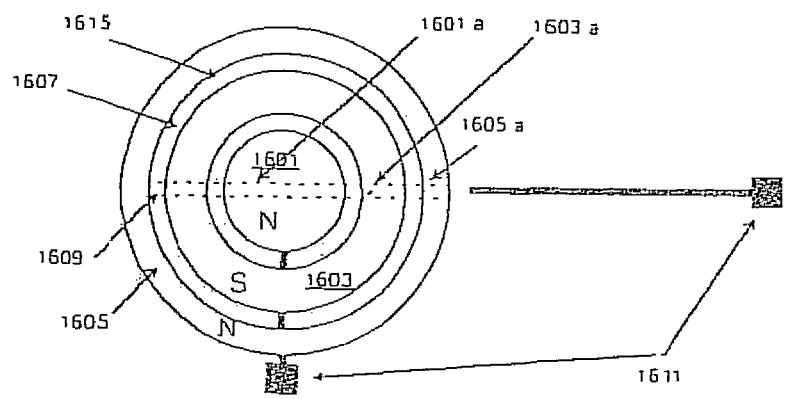
FIG. 16 is a planar view illustrating a mixed pole array of the present invention operative in the absence of a backer plate using an assembly pin to maintain orientation and gaps between magnets.

FIG. 16 illustrates a first magnet 1601 having a North orientation aligned relative to a second magnet 1603 and a third magnet 1605 having a North orientation. Blank spaces or air gaps 1607 and 1609 are maintained between adjacent magnets. It is appreciated that the blank space or air gaps 1607 and 1609 are each independently optionally filled with a nonmagnetic element as detailed above or a nonferrous metal. An assembly pin 1611 simultaneously engages at least two magnets 1601, 1603, and 1605 and at least one gap 1607 and 1609 so as to retain magnetic pole orientation of the aforementioned magnets. Each of the magnets is so retained in a relative position as a complementary bore denoted at 1601a, 1603a, and 1605a, for the magnets 1601, 1603, and 1605, respectively. Alternatively, or in combination with a pin 1611, a rubber grommet is provided at 1615 that fills gap 1607 and retains the position of magnets 1601 and 1603. Through the inclusion of bore holes in the grommet 1615 (not shown) and aligned with 1601a and 1603a, the pin 1611 can operate in conjunction with the grommet 1615. It is noted that the orientation of a given magnet 1601, 1603, or 1605 is readily reversed by disengaging assembly pin 1611 from the array, reversing the orientation of a magnet, and reinserting assembly pin 1611 to achieve a different therapeutic effect from the same array of magnets making up the inventive magnetic apparatus. While FIG. 16 depicts the magnets 1601, 1603, and 1605 as a concentric array, it is appreciated that the magnets of an inventive magnet apparatus can be formed in a variety of geometric patterns including parallel strips and can also be formed into geometric shapes to tile a two-dimensional surface with such geometric shapes illustratively including triangles, squares, circles, ellipse, square, triangle, rectangle, star, heart, kidney, or higher polygons, and combinations thereof.

Figure 17:
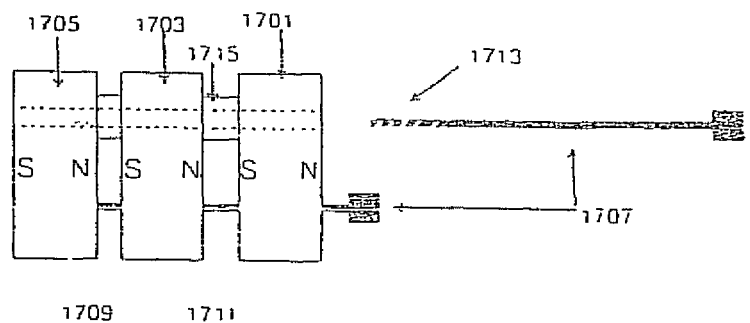
FIG. 17 is a planar view illustrating a mixed pole array of the present invention operative in the absence of a backer plate using a threaded fastener to maintain orientation and gaps between magnets.

FIG. 17 illustrates an inventive magnetic apparatus in which magnets 1701, 1703, and 1705, each having a bore therein, are adapted to receive a threaded fastener 1707 so as to retain the magnets 1701, 1703, and 1705 in a relative spaced-apart position with gaps 1709 and 1711 therebetween. One such fastener 1707 is depicted in simultaneous engagement while a second such fastener is shown in exploded view to illustrate a threaded portion 1713 that engages complementary threads in magnet 1705. Nonmagnetic or nonferrous metal spacers 1715 are provided to maintain the magnets 1701, 1703, and 1705 in a preselected spaced-apart relationship.

Figure 18:
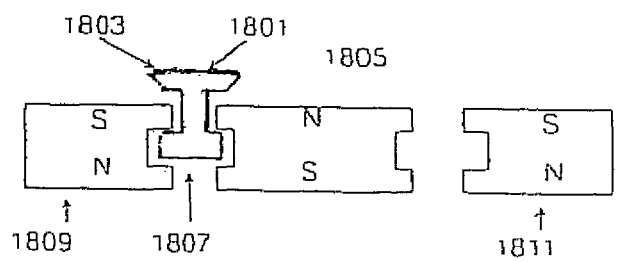
FIG. 18 is a planar view illustrating a mixed pole array of the present invention operative in the absence of a backer plate using a key lock to maintain orientation and gaps between magnets.

FIG. 18 illustrates an alternative embodiment of a magnetic apparatus relative to FIG. 16 for maintaining an array of magnets in relative position with air gaps therebetween. A mechanical key 1801 has a knurled or screw head top 1803, a shaft 1805, and a locking element 1807. The key 1801 engages a space formed by the proximal engagement of magnets 1809 and 1811, each of which being machined to receive the shaft 1805 and locking element 1807 in a first position and the magnets 1809 and 1811 being locked in position upon rotation of the key 1801. It is noted that by flipping one of the magnets 1809 or 1811, the apparatus so depicted is reconfigured to provide a different therapeutic effect.

Figure 19A:
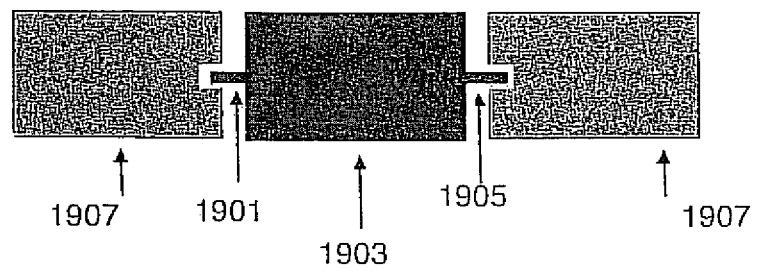
FIG. 19A is a cross sectional view illustrating a mixed pole array of the present invention operative in the absence of a backer plate using a mechanical interlock to maintain orientation and gaps between magnets.
Figure 19B:
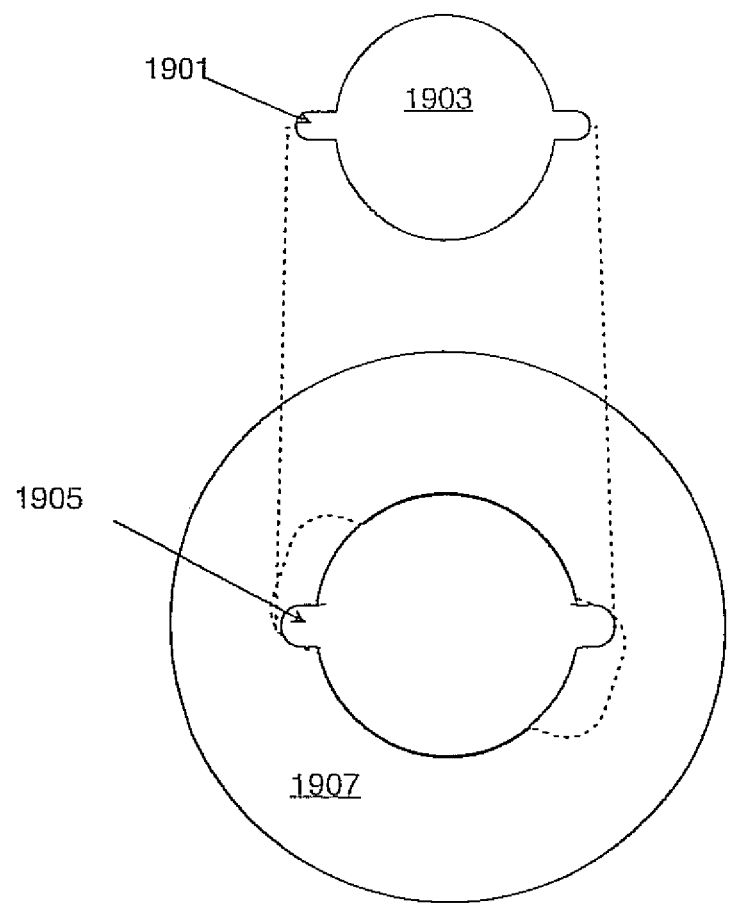
FIG. 19B is a top view of the array shown in FIG. 19A.

FIGS. 19A and B illustrate a reconfigurable magnet apparatus particularly well suited for a concentric magnet array in which the individual magnet elements are machined to form a projecting tab 1901 in a first magnet 1903. The tab 1901 engages a complementary cutout 1905 in a second magnet 1907 such that upon the first magnet 1903 being rotated through a given angle of, for example, 90 degrees, the magnets 1903 and 1907 shift from unlocked to locked relative position. It is noted that through inversion of magnet 1903, that the depicted magnet apparatus is reconfigured for different therapeutic effect.

A user-configurable array of magnets forming a therapeutic magnetic apparatus is operative using a flexible magnet having a strength of between 0.5 and approximately 2 MGOe, ceramic magnets of strength of approximately 3 MGOe, neodymium magnets of strength of approximately 50 MGOe, other magnetic materials, and combinations thereof. It is appreciated that in particular therapeutic applications the ability to tailor magnetic field strength through a combination of such magnets is deployed with a magnet apparatus to tailor field properties for therapeutic or clamping applications.

Having described embodiments for a therapeutic magnet apparatus, it is noted that modifications and variations can be made by persons skilled in the art in light of the above teachings. It is therefore to be understood that changes may be made in the particular embodiments of the invention disclosed which are within the scope and spirit of the invention as defined by the appended claims.

The invention claimed is:

1. A process for adjusting a magnetic field characteristic projecting from a magnetic treatment apparatus comprising:
    laying out a plurality of planar magnets having a planar geometric shape in a rigid flat planar pattern, each of said plurality of planar magnets that range in pole width from ½ to 2 inches across with a nominal thickness of 0.060 to 0.150 inches oriented with pole face perpendicular toward the body in a treatment orientation, said plurality of magnets having a total weight of less than one International pound, with a first magnet of said plurality of magnets positioned with north flux positioned adjacent to a south flux of a second magnet of said plurality of magnets, said plurality of magnets being semi-circular magnets or nested planar geometric shapes arranged with their side walls abutting adjacent elements, and having pole faces oriented into nested groupings of alternating polarity pole faces with said nested groupings of alternating polarity pole faces oriented perpendicular toward the body in a treatment orientation such that the magnetic field characteristic projecting from said plurality of magnets is applied perpendicularly to a treatment subject;
    repositioning one of said plurality of magnets to define a reoriented array to adjust the magnetic field characteristic projecting from the magnetic apparatus relative to the pattern of said plurality of magnets; and
    applying said reoriented array to, or proximal to a treatment subject.

2. The process of claim 1 wherein said reoriented array is a planar array.

3. The process of claim 1 further comprising simultaneously engaging at least two of said plurality of magnets with a mechanical fastener.

4. The process of claim 3 wherein said mechanical fastener is a ferromagnetic backing plate to which said plurality of magnets are attached.

5. The process of claim 1 further comprising creating a gap filled with a magnetically transparent spacer or a magnetically permeable spacer between at least two of said plurality of magnets.

6. The process of claim 1 wherein the treatment subject is an animal, water, food, or a plant.

\* \* \* \* \*